United States Patent
Miller et al.

(10) Patent No.: US 6,859,968 B2
(45) Date of Patent: Mar. 1, 2005

(54) NODAL MOUNTED SYSTEM FOR DRIVING A POWER APPLIANCE

(75) Inventors: Kevin A. Miller, Bellevue, WA (US); John W. Pace, Bothell, CA (US); Aafke G. Koster, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 236 days.

(21) Appl. No.: 10/179,741

(22) Filed: Jun. 24, 2002

(65) Prior Publication Data

US 2004/0000016 A1 Jan. 1, 2004

(51) Int. Cl.$^7$ ............................................... A61C 17/34
(52) U.S. Cl. ............................ 15/22.1; 310/50; 310/80
(58) Field of Search ................................ 15/22.1, 22.2, 15/22.3, 22.4, 23; 310/50, 80, 81

(56) References Cited

U.S. PATENT DOCUMENTS

| | | | | |
|---|---|---|---|---|
| 3,945,076 A | * | 3/1976 | Sung | 15/22.1 |
| 5,189,153 A | * | 2/1993 | Gregory et al. | 540/122 |
| 5,263,218 A | * | 11/1993 | Giuliani et al. | 15/22.1 |
| 5,613,259 A | * | 3/1997 | Craft et al. | 15/22.1 |
| 5,796,325 A | * | 8/1998 | Lundell et al. | 336/233 |
| 6,140,723 A | * | 10/2000 | Matsui et al. | 310/81 |
| 2002/0084707 A1 | * | 7/2002 | Tang | 310/81 |

* cited by examiner

Primary Examiner—Robert J. Warden, Sr.
Assistant Examiner—Shay Balsis

(57) ABSTRACT

The power toothbrush, which has a rotating brushhead movement, includes a housing with a motor mounted therein having an armature which in operation rotates through an arc of predetermined magnitude. The toothbrush also includes a brushhead mounted on a shaft which is connected to an output mass. A spring assembly couples the armature to the output mass, the spring assembly including two spring portions with a node point therebetween, wherein when the armature rotates, the brushhead moves in an opposite direction. The frequency of the movement of the armature is set equal to the resonant frequency of the spring coupling system and the output assembly.

12 Claims, 4 Drawing Sheets

US 6,859,968 B2

NODAL MOUNTED SYSTEM FOR DRIVING A POWER APPLIANCE

TECHNICAL FIELD

This invention relates generally to resonant drive systems for power toothbrushes and similar appliances, and more specifically concerns such systems having a rotational motor with a spring coupling arrangement from the motor to an output element, such as a brushhead.

BACKGROUND OF THE INVENTION

Power toothbrushes are in general well known and encompass a wide variety of designs and physical arrangements. Some power toothbrushes have proven to be both effective and commercially successful. One example is the toothbrush shown in U.S. Pat. No. 5,189,751, which is owned by the assignee of the present invention.

Many power toothbrushes have a rotary-type motion. Some have the capability of a 360° armature rotation, but due to design arrangements produce an oscillatory movement limited to a particular range of motion, i.e. a selected arcuate portion of 360°, in order to provide a more suitable brushing effect. Some of these rotary motion devices are mechanically driven, while others are resonant systems, involving a movable mass such as a brushhead structure and a spring which is attached to the handle. The resonant frequency of the system is affected by the handle.

The present invention is concerned with resonant systems. Resonant devices, using a motor with a rotating armature, often have the advantages of design simplicity and reasonable cost, as well as generally a small size, but also have significant disadvantages, including vibration coupled to the handle of the device caused by the reversing action of the system as it oscillates back and forth through the selected arc, instead of rotating continuously through a 360° rotation. The vibration is coupled to the handle through the spring element. The resonant frequency of such a system is affected by the moment of inertia (MOI) of the handle, as well as the other parts of the drive system. Performance of the device is also affected by the dynamics of the handle, such as damping, spring rate and moment of inertia. Further, when a user grips the handle of such a simple resonant system device, the user becomes part of the system, which further changes the dynamics of the handle and the resulting performance of the device. Thus, in a resonant system, many variables affect the dynamic characteristics of the handle and system performance. In addition, the spring coupling to the handle in a resonant system produces a significant physical vibration in the handle. These disadvantages have affected the commercial success of such toothbrushes.

It is thus desirable to significantly reduce the physical vibration in the handle and the noise produced by such a resonant drive system as well as increasing the efficiency of such a system.

DISCLOSURE OF THE INVENTION

Accordingly, the present invention is a power toothbrush, or other similar appliance, comprising: a toothbrush housing; a drive assembly which comprises: a motor having an armature which in operation rotates back and forth through an arc of predetermined magnitude; an output assembly which includes a brushhead; a coupling assembly having a node point, wherein the coupling assembly connects the armature to the output assembly and wherein the coupling assembly operates in response to a drive signal having such a frequency that the toothbrush operates in a mode in which the brushhead rotates 180° out of phase from the rotation of the armature, such that the drive assembly is substantially isolated vibrationally from the housing; and at least one support element connected between the drive assembly and the housing, wherein the node point remains substantially stationary during operation of the toothbrush.

BEST MODE FOR CARRYING OUT THE INVENTION

Figure 1:
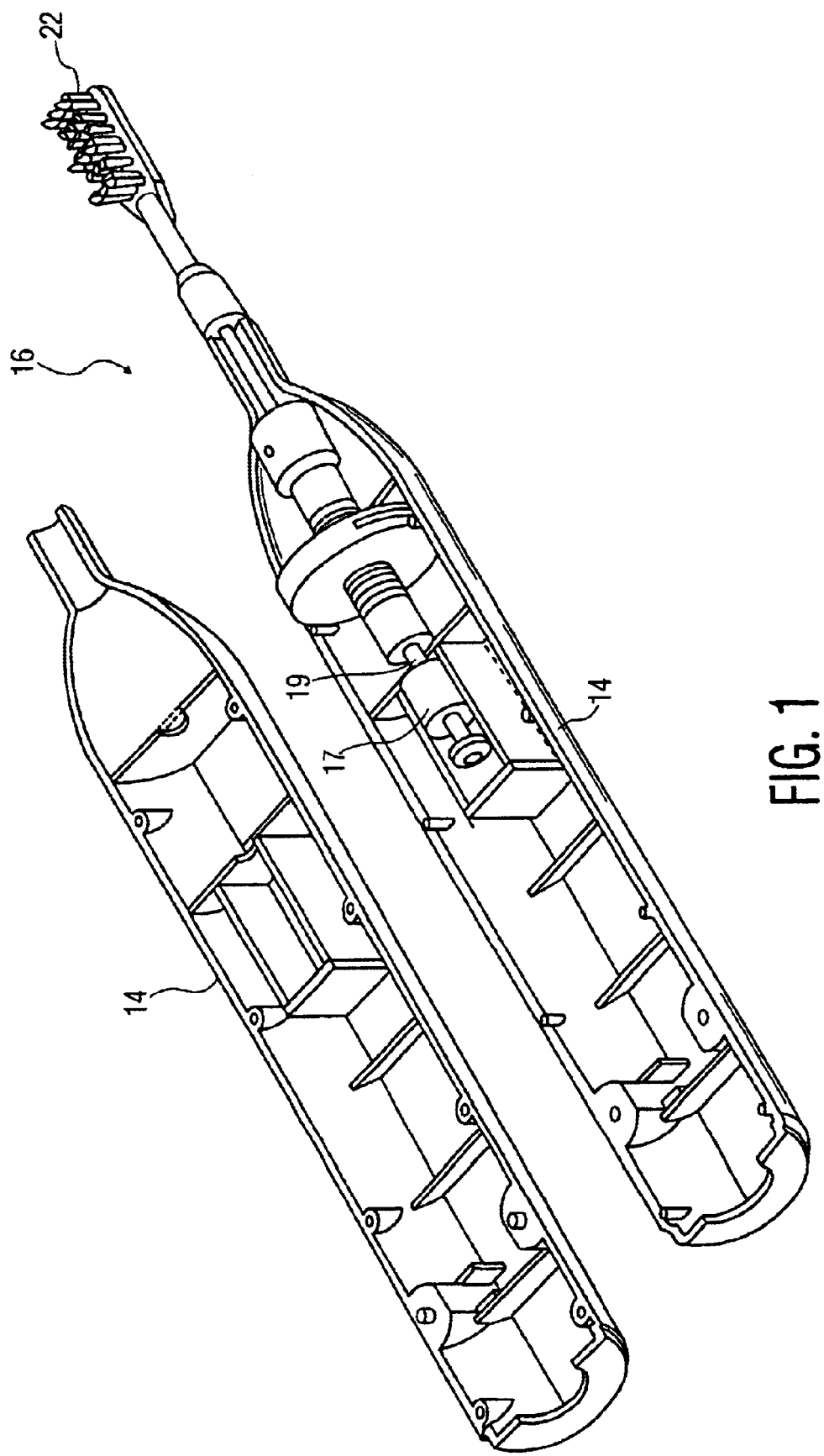
FIG. 1 is an elevational view showing the major portions of the drive system of the present invention.
Figure 2:
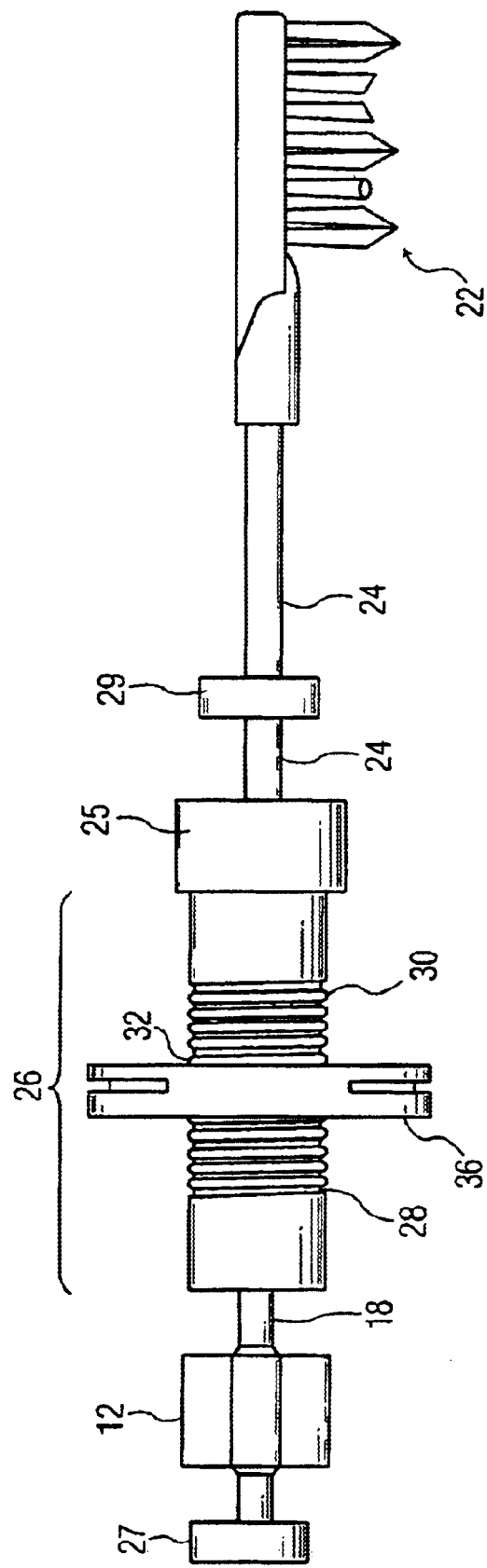
FIG. 2 is a perspective view showing the drive system of the present invention in the context of a power toothbrush.

Referring to FIGS. 1 and 2, a small appliance motor 12 is mounted in a housing or handle 14 (shown split) of a power toothbrush 16. Although the present invention is described in the context of a power toothbrush for convenience of explanation and illustration, it should be understood that the system of the present invention could be used in other small appliances which drive other workpiece elements.

Motor 12 includes an armature 18 which is driven in a rotational mode in response to an electrical current provided from a battery 20 to a stator portion (not shown) of motor 12. Battery 20 will typically be a rechargeable battery, recharged via a charging base (not shown) in which the toothbrush is positioned when not in use. Such a charging base arrangement, for instance, is shown in U.S. Pat. No. 5,796,325, which is also owned by the assignee of the present invention.

At the other end of the drive system from motor 12 is a workpiece element, such as a brushhead 22. For the purposes of this invention, brushhead 22 can take various configurations. Brushhead 22 is mounted on an elongated shaft 24, which extends rearwardly from the brushhead 22 to an output mass 25, located in housing 14. The present invention, as indicated above, is a resonant system, one characteristic of which is that the drive system is driven by the motor at a frequency which is at or very close to the resonant frequency of the mechanical drive system. This increases the efficiency of the system, as well as providing other performance benefits.

The resonant system of the present invention includes a spring assembly, shown generally at 26, which couples motor armature 18 to the output mass 25. Bearings 27 and 29 support the motor and the output shaft within the housing. Spring assembly 26 in the embodiment shown comprises a helical spring which is divided into two series portions 28 and 30, separated by an intermediate node point 32. The two spring portions 28 and 30 in the embodiment shown are substantially equal, having spring constants k1 and k2, respectively. At node point 32 is located a mounting spring element 36, also referred to a centering spring, which mounts, i.e. connects, the spring assembly 26 to housing 14. Mounting spring 36 also has a small damping effect on the action of the spring assembly.

As indicated, spring portions 28 and 30 typically comprise a single spring structure which includes a node region where the centering spring element 36 is mounted. The arrangement shown has the advantage of isolating the drive system from the housing, such that there is little or no vibration transmitted to the housing.

The helical spring portions 28 and 30 in the embodiment shown could be different spring arrangements, including a wire-wrapped coil spring or leaf or beam springs, or a torsion element, again with a node point between two series portions thereof. The centering spring 36 (with some damping effect) could be made from a number of different materials, including rubber, and could take various configurations, including a thick washer-like configuration. The centering spring 36, being positioned at the node point between the two spring portions, will not move substantially during operation of the device, and there will be very little or no vibration coupled from the drive system to the housing. The centering spring 36 also insures alignment of the brushhead arrangement and the motor during operation of the device.

In normal operation of the present resonant system, the drive frequency will be approximately equal to the resonant frequency of the drive system. In this mode, the brushhead portion is rotating 180° out of phase with the motor. Referring now to FIG. 2, spring portion 30 is connected at its far end to output mass 25 which has a moment of inertia j2, which in turn is connected to brushhead shaft 24. Armature 18 has a moment of inertia J1. The combination of brushhead shaft 24 and brushhead 22 has a moment of inertia J3. In the embodiment shown, if the spring constants k1, k2 of the two spring portions 28, 30 are equal, and if the moment of inertia J1 of the motor armature 18 equals the sum of the moments of inertia of mass 25 (J2) and the combination of the shaft and the toothbrush (J3), such that k1=k2 and j1=j2+j3, the resonant frequency ω of the drive system will be approximately:

$$\omega = \sqrt{\frac{k1}{j1}} \cdot \text{or } \omega = \sqrt{\frac{k2}{j2+j3}}$$

If the motor is driven in this mode (the resonant frequency mode), then the unloaded brushhead 22 will move through the same arc (the same brushhead amplitude) as the motor armature 18, but in the opposite rotational direction, i.e. 180° out of phase, from the rotation of the armature. Operating the motor at the resonant frequency of the drive system will produce an efficient system, i.e. significant power is delivered to the brush element at the resonant frequency. Further, there is little or no vibration of the drive system coupled to the housing; i.e. the resonant drive system is isolated from the moment of inertia of the housing and also the user (by virtue of the user's grip, which can vary). The moment of inertia of the drive (armature) end of the system in the nodal mount arrangement of FIG. 2 works against the moment of inertia of the driven (brushhead) end to produce this desirable vibration isolation effect.

While the embodiment of FIG. 2 teaches two spring portions 28 and 30, it should be understood that the spring assembly 26 could be implemented with a single spring. In such a case, the node point is located approximately halfway down the length of the spring for the mounting of spring 36. As indicated above, spring element 36 can be made from various damping materials and is mounted directly to housing 14. Spring element 36 can be a torsional spring, having a spring constant of k3, connected between node point 32 and housing 14. Again, the torsional spring provides a centering (alignment) function for the motor and the load (brushhead).

Various alternatives to the above-described arrangement are possible. For instance, if it is desired that the amplitude of the brushhead or other workpiece element be different from the amplitude of the motor armature, the ratio of the moment of inertia for the armature (j1) and the total of the moments of inertia for the output mass (j2) and the shaft and brushhead (j3) is made to be other than 1.0. The node point along the spring assembly will then occur at a point other than halfway along the length thereof. As one example, in order to have the brushhead have approximately half the amplitude of the motor amplitude, j1=0.5 (j2+j3) and k1=0.5 k2. Other selected values of spring constants and moments of inertia will result in other amplitude ratios.

In addition, it may be desirable to have a vibration effect which is noticeable to the user at selected times in the use of the toothbrush, for instance, after a certain period of use time (e.g. 2 minutes). This requires that the device operate in a different torsional mode, referred to as a vibration mode. In this mode, the rotation of the brushhead end of the system is in phase with the rotation of the drive (motor) end of the system, working against the handle. This vibration mode of operation results when the motor frequency (the drive signal) has a frequency which is significantly different than the resonant frequency of the coupling system. The frequency at which this happens for a particular system can be determined by one skilled in the art. The device is programmed such that when an event occurs which is to be signaled to the user, such as a timer signal, the drive frequency is changed so that the device operates in its vibrational mode. In this mode, as noted above, significant vibration from the drive system is coupled to the housing 14 through centering spring element 36. This coupling of vibration to the housing 14 provides a physical indication (feedback) to the user of the occurrence of selected operating conditions, such as time of use or brushing pressure, measured by other portions of the system.

Figure 4:
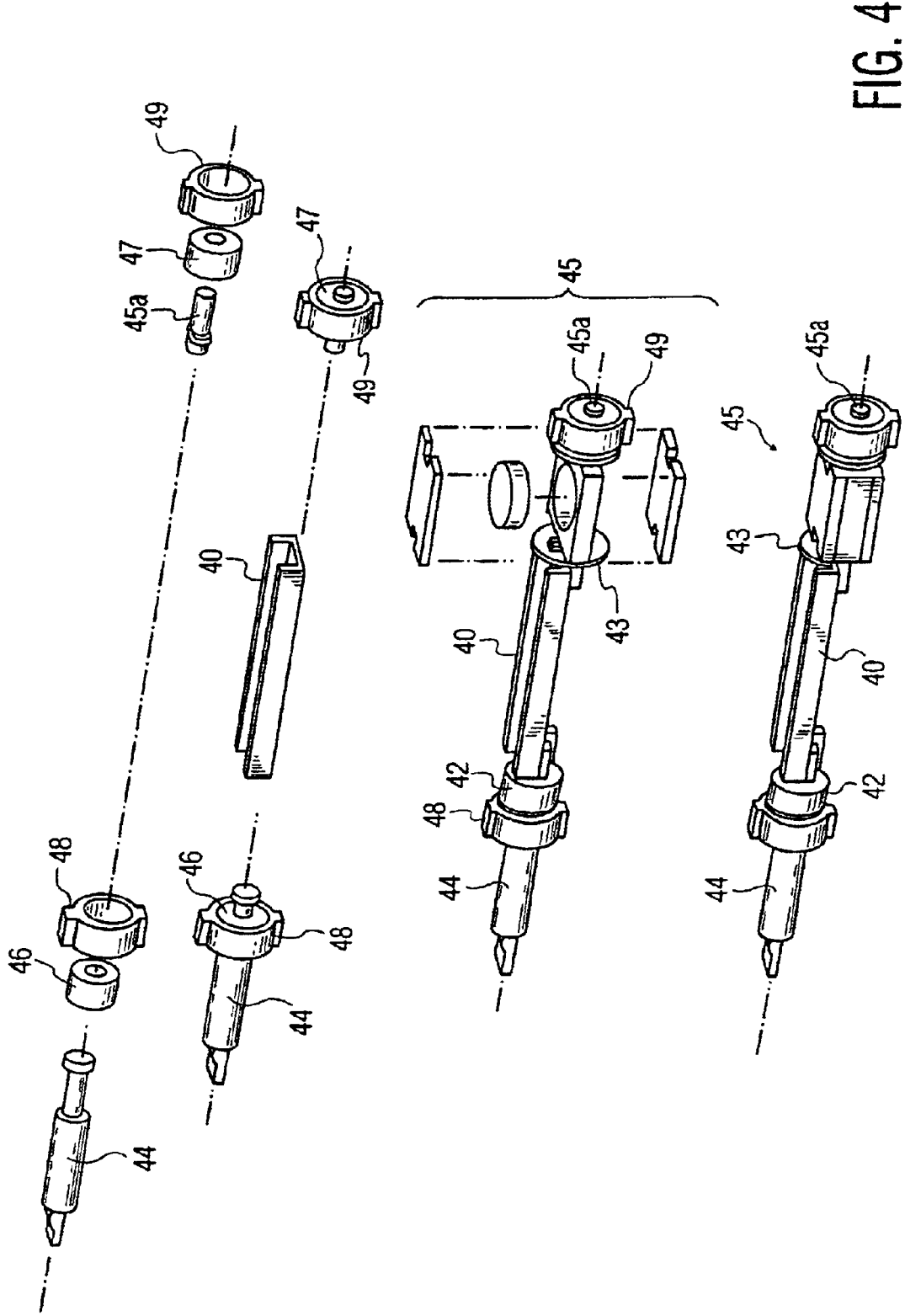
FIG. 4 is a perspective view of an alternative embodiment of the system of the present invention.

Another embodiment of the nodal mounted system of the present invention is shown in FIGS. 4A and 4B. This other embodiment uses a torsional element 40, instead of a spring assembly 26. The torsional element is stiff in all directions except for one, the desired twisting or rotational action. While a U-shaped channel is shown as an example of such a torsional member, other cross-sectional shapes could be used, such as for instance a V shape, or other cross-sectional shape. The V shape mass may have some advantage over the U shape in mounting to the motor and brushhead portions of the system. In the embodiment shown, the respective ends of the torsional element 40 are mounted in elastomeric end pieces 42 and 43. A mounting shaft 44 extends from elastomeric end piece 42. Mounting shaft 44 supports a brushhead assembly (not shown) or other workpiece. Elastomeric end piece 43 is positioned at the motor (drive) end of the device. The motor is represented at 45. A pin 45A extends from the armature of the motor so that the motor end of the device can be supported to the housing. Mounting shaft 44 and pin 45A are supported by elastomeric support elements 46 and 47. The support elements provide radial and rotational alignment for the device as well as support.

The support elements are fixed to their associated shaft/pin members. In operative action, cage members 48, 49 hold the outside portions (surfaces) of the support elements fixed, while the inner portion of each support element attached to the shaft winds up in a spring-like fashion by virtue of the rotation of the armature shaft. This arrangement, when driven at the resonant frequency of the drive assembly, results in the armature rotating in one direction while the brushhead shaft rotates in the opposite direction. A "virtual"

node point occurs at a point along element 40, with the vibrational torques applied to the housing by cage members 48, 49 effectively canceling each other.

Figure 3:
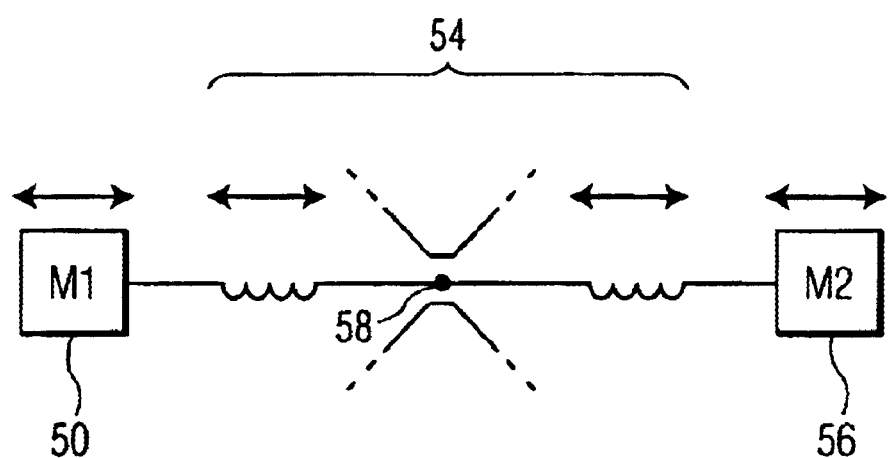
FIG. 3 is a simplified view of a linear spring arrangement.

It should also be understood that workpiece element motions other than rotational can be accomplished using a similar coupling spring approach to that of FIG. 2. For instance, a linear longitudinal motion of a brushhead or similar element can be produced using a compression spring which is operated in an axial mode. Referring to FIG. 3, a driving mass 50 can be moved linearly by means of various motor arrangements, which drives one end of the spring assembly 54, resulting in a movement of the driven element 56, i.e. the brushhead, with the movement of the driving mass. The driving mass and the driven mass thus will move in opposite directions. As with the embodiment of FIG. 1, there is a specific point along the spring element which will not move during operation of the device. This is node point 58. Similar effects can be produced using a spring and node point arrangement where a driving mass is moved laterally about the node point, which action is then transferred via the second portion of the spring to a driven mass. The two motions are 180° out of phase.

Thus, in the present invention, a motor is used to drive an armature through a selected amplitude or arc. The action of the armature is coupled to a workpiece element, such as a brushhead, through a coupling arrangement which in one embodiment comprises two torsion spring portions, which have a node point between them. Driving the system at the resonant frequency results in the workpiece element following the action of the armature, but approximately 180° out of phase. Efficient power transfer also occurs to produce effective action of the workpiece element. In another embodiment a torsional element, such as a U channel or V channel, is used instead of a spring member, producing a virtual node at a point along its length. While the invention has been described in the context of a toothbrush, it should be understood that the same arrangement can be used for other small appliances.

Although a preferred embodiment of the invention has been disclosed here for purposes of illustration, it should be understood that various changes, modifications and substitutions may be incorporated without departing from the spirit of the invention, which is defined by the claims which follow.

What is claimed is:

1. A power toothbrush, comprising:

a toothbrush housing;

a drive assembly comprising: a motor having an armature which in operation rotates back and forth through an arc of predetermined magnitude about the longitudinal axis of the armature; an output assembly which includes a brushhead; a coupling assembly having a node point, the coupling assembly connecting the armature to the output assembly, wherein the coupling assembly is so arranged relative to the armature and the output assembly and operates in response to a drive signal having such a frequency that the brushhead rotates about the longitudinal axis of the armature 180° out of phase from the rotation of the armature, such that the drive assembly is substantially isolated vibrationally from the housing; and at least one support element connected between the drive assembly and the housing, wherein the node point of the coupling assembly remains substantially stationary without rotating during operation of the toothbrush.

2. The toothbrush of claim 1, wherein the motor is driven at a frequency which is approximately equal to the resonant frequency of the drive assembly.

3. The toothbrush of claim 2, wherein the coupling assembly is a spring member and wherein the support element extends between a node point on the spring member and the housing, thereby defining two spring members along the length thereof.

4. The toothbrush of claim 3, wherein the two spring portions are substantially equal in length, with approximately equal spring constants.

5. The toothbrush of claim 3, wherein the armature has a moment of inertia which is approximately equal to the moment of inertia of the output assembly.

6. The toothbrush of claim 1, wherein the output assembly comprises an output mass and a brushhead shaft extending from the output mass, on an outer end of which is mounted the brushhead.

7. The toothbrush of claim 1, wherein the armature and the brushhead move through approximately the same arc.

8. The toothbrush of claim 1, wherein the brushhead moves through an arc which is different in magnitude than the arc of the armature.

9. The toothbrush of claim 1, wherein in operation of the toothbrush, the node point does not move substantially relative to the housing and wherein the support element is a spring element which has some damping effect.

10. The toothbrush of claim 1, including a motor control circuit for selectively changing the frequency of the drive signal, such that the toothbrush operates in a mode in which the brushhead rotates phase with the armature, resulting in vibration of the drive assembly being coupling to the handle, providing a signal to the user of said selected occurrence.

11. A power appliance, comprising:

an appliance housing;

a drive assembly, comprising: a motor having an armature which in operation oscillates through an arc of predetermined magnitude about the longitudinal axis of the armature; an output assembly which includes a workpiece element; a coupling assembly having a node point, the coupling assembly connecting the armature to the output assembly, wherein the coupling assembly is so arranged relative to the armature and the output assembly and operates in response to a drive signal of a selected frequency such that the workpiece rotates about the longitudinal axis of the armature 180° out of phase from rotation of the armature, wherein the drive assembly is thus substantially isolated vibrationally from the housing; and a support element connected between the node point and the housing, wherein in operation of the appliance, the node point remains substantially stationary, without rotation.

12. An appliance of claim 11, wherein the motor is driven at a frequency which is approximately equal to the resonant frequency of the drive assembly.

* * * * *